United States Patent
Morris et al.

(10) Patent No.: US 6,750,251 B2
(45) Date of Patent: Jun. 15, 2004

(54) HALF-SANDWICH RUTHENIUM (II) COMPOUNDS COMPRISING NITROGEN CONTAINING LIGANDS FOR TREATMENT OF CANCER

(75) Inventors: Robert Edward Morris, Eire (IE); Peter John Sadler, Penicuik (GB); Haimei Chen, Edinburgh (GB); Duncan Jodrell, Edinburgh (GB)

(73) Assignee: The University Court, The University of Edinburgh (UK), Edinburgh (GB)

( * ) Notice: Subject to any disclaimer, the term of this patent is extended or adjusted under 35 U.S.C. 154(b) by 0 days.

(21) Appl. No.: 10/134,404

(22) Filed: Apr. 26, 2002

(65) Prior Publication Data

US 2003/0023088 A1 Jan. 30, 2003

Related U.S. Application Data

(63) Continuation of application No. PCT/GB00/04144, filed on Oct. 26, 2000.

(51) Int. Cl.$^7$ .................. C07F 17/02; A61K 31/555; A61K 31/295; A61P 35/00
(52) U.S. Cl. .................. 514/492; 514/188; 556/137; 546/2
(58) Field of Search .............. 556/137; 546/2; 514/188, 492

(56) References Cited

U.S. PATENT DOCUMENTS

| | | | |
|---|---|---|---|
| 4,699,978 A | 10/1987 | Barton | 536/27 |
| 4,843,069 A | 6/1989 | Keller et al. | 514/184 |
| 4,980,472 A | 12/1990 | Tomcufcik et al. | 544/405 |
| 5,225,556 A | 6/1993 | Barton | 546/88 |
| 5,386,044 A | 1/1995 | Dembek | 556/13 |
| 5,708,022 A | 1/1998 | Bastos et al. | 514/492 |

FOREIGN PATENT DOCUMENTS

| | | | | |
|---|---|---|---|---|
| JP | 11209314 | | 8/1999 | |
| JP | 11209314 A | * | 8/1999 | C07C/13/263 |
| WO | WO 86/00804 | | 2/1986 | |
| WO | WO 96/13510 | | 5/1996 | |
| WO | WO 200130790 A1 | * | 5/2001 | A61K/33/24 |
| WO | WO 200202572 A1 | * | 1/2002 | A61K/33/24 |
| WO | WO 02/40494 A1 | | 5/2002 | |

OTHER PUBLICATIONS

Yann Hung, Inorganic Chemistry 20(2), 1981 pp 457–463.*
Robert E. Morris, et al J. Med. Chem.; 2001; 44(22) pp 3616–3621.*
Susan S. Alguindigue, et al Organometallics; 1999; 18(24) pp 5112–5119.*
Fred B. McCormick, Organometallics 12(3), 1993 pp 610–612.*
Roger Mahe, J. Organic Chemistry 54(7), 1989 pp 1518–1523.*
Cetinkaya, Journal of Materials Chemistry 8(8) 1835–1838, 1988.*
Arthur, J. Organometallics Chemistry 208(3) 369–387 1981.*
Aird, British. J. Cancer 86, 1652 (2002).*
Aird et al., "RM175, A Novel Ruthenium (Ru$^{11}$) Organo-Metallic Complex: Patterns of Resistance in Vitro and in Vivo" Br. J. Cancer 85(supp. 1), 2001.
Allardyce et al., "Ruthenium in Medicine: Current Clinical Uses and Future Prospects" Platinum Metals Rev. 45(2):62–69, 2001.
Carmona et al., "Synthesis, X–Ray Structure, and Nuclear Magnetic Resonance . . . " J. Chem. Soc., pp. 1463–1476, 1990.
Harvey, "1,4,9,10–Tetrahydroanthracene From the Stepwise Reduction of . . . " J. Org. Chem. 32:238, 1967.
Pandey et al., "Synthesis and Characterization of." Indian J. of Chem. 35A:434–437, 1996.
Aird et al., "*In vitro and in vivo* activity and cross resistance profiles of novel ruthenium (II) organometallic arene complexes in human ovarian cancer," British Journal of Cancer 86:1652–1657 (2002).
Aronson et al., "The Reactions of [Ru(n$^6$–arene)Cl$_2$]$_3$ Compounds with a Series of Aminopyridine Ligands:X–Ray Crystal Structures of [Ru(n$^6$–1,4–MeC$_6$H$_4$CHMe$_2$)Cl$_2$(NC$_5$H$_4$NH$_2$)] And [Ru(n$^6$–C$_{16}$H$_{16}$)CL$_3$(NC$_5$H$_4$NH$_2$)]," Polyhedron 10(15):1727–1732 (1991).
Beasley et al., "Complexation of 1,4,5,8,9,10–Hexahydroanthracene (HHA) to Iron or Ruthenium: A Bis(diene) diiron HHA Geometry, Hydroaromatic Ruthenium Compounds Related to Ru(n$^6$–THA)Cl$_2$(DMSO) (THA = 1,4,9,10–Tetrahydroanthracene; DMSO = Dimethyl Sulfoxide), and Ru$_3$(CO)$_{12}$–Catalyzed HHA Rearrangements," Organometallics 12:4599–4606 (1993).
Bennett et al., "Arene Ruthenium(II) Complexes formed by Dehydrogenation of Cyclohexadienes with Ruthenium(III) Trichloride," J.C.S. Dalton 233–241 (1974).

(List continued on next page.)

*Primary Examiner*—Mark L. Berch
(74) *Attorney, Agent, or Firm*—Fish & Richardson P.C.

(57) ABSTRACT

Compounds which may be used in the treatment and/or prevention of cancer have the formula (I) wherein: $R^1$, $R^2$, $R^3$, $R^4$, $R^5$ and $R^6$ independently represents H, alkyl, —CO$_2$R', aryl or akylaryl, which latter two groups are optionally substituted on the aromatic ring; R' represent alkyl, aryl or alkaryl; X is halo, H$_2$O, (R')(R")SO, R'CO$_2$— or (R')(R")C=O, where R" represents alkyl, aryl or alkaryl; Y is a counterion; m is 0 or 1; q is 1, 2 or 3; C' is C$_1$ to C$_{12}$ alkylene, optionally substituted in or on the alkylene chain, bound to two A groups; p is 0 or 1 and r is 1 when p is 0 and r is 2 when p is 1; and A and B are: each independently N–donor nitrile ligands; or B is halo and A is an N–donor pyridine ligand, optionally substituted at one or more of the carbon atoms of the pyridine ring; or p is 0, A is NR$^7$R$^8$ and B is NR$^9$R$^{10}$, wherein R$^7$, R$^8$, R$^9$ and R$^{10}$ independently represent H or alkyl, and A and B are linked by an alkylene chain, optionally substituted in or on the alkylene chain, or p is 1, A is NR$^7$ and B is NR$^9$R$^{10}$, wherein R$^7$, R$^9$ and R$^{10}$ are as previously defined, and A and B are linked by an alkylene chain, optionally substituted.

12 Claims, No Drawings

OTHER PUBLICATIONS

Bennett et al., "Mono–and bis–(acetylacetonato) complexes of arene–ruthenium(II) and arene–osmium(II): variation of the binding mode of η–acerylacetonate with the nature of the arene," Can. J. Chem. 79:655–669 (2001).

Carmona et al., "Synthesis, X–Ray Structure, and Nuclear Magnetic Resonance ($^1$H and $^{13}$C) Studies of Ruthenium(II) Complexes containing Pyrazolyl Ligands," J. Chem. Soc. Dalton Trans. 1463–1476 (1990).

Cetinkaya et al., "Antibacterial and Antifungal Activities of Complexes of Ruthenium(II)," Arzneim.–Forschl/Drug Res. 49(1)(6):538–540 (1999).

Chen et al., "Organometallic Ruthenium(II) Diamine Anticancer Complexes: Arene–Nucleobase Stacking and Stereospecific Hydrogen–Bonding in Guanine Adducts," J. Am. Chem. Soc. 124(12):3064–3082 (2002).

Clarke et al., "Non–Platinum Chemotherapeutic Metallopharmaceuticals," Chem. Rev. 99:2511–2533 (1999).

Crabtree et al., "Arene–Ruthenium Complexes Containing Nitrogen Donor Ligands," Journal of Organometallic Chemistry 141:325–330 (1977).

Cummings et al., "Novel ruthenium (Ru$^{11}$) organo–metallic complexes: in vitro cytotoxicity in wild type and drug resistant A2780 human ovarian cancer cell lines," Clinical Cancer Research 6 (Suppl.) (2000).

Dale et al., "Studies on DNA damage and induction of SOS repair by novel multifunctional bioreducible compounds. II. A metronidazole adduct of a ruthenium–arene compound," Anti–Cancer Drug Design 7:3–14 (1992).

Drew et al., "Transition Metal–Diene Complexes. Part 4. The Crystal and Molecular Strcture and Isomerization of η–Cyclopentadienyl (η–3–methoxycarbonyl–cyclohexa–1,4–diene)rhodium(J)," J.C.S. Dalton :1034–1040 (1981).

Elsegood et al., "The synthesis of new paracyclophane complexes of ruthenium(II): Crystal structure of [Ru(η$^6$–C$_{16}$H$_{16}$)Cl(C$_5$H$_5$N)$_2$][PF$_8$]," Journal of Organometallic Chemistry 356:C29–C31 (1988).

Garcia et al., "Reactivity of [{(η$^6$–arene)RuCl($\mu$–Cl)}$_2$] towards some potentially bientate ligands. Molecular structure of [(η$^6$–p–cymene)RuC](taz)PF$_5$(p–cymene = p–MeC$_8$H$_4$CH–ME$_2$; taz = 2,6–dimethyl–5–oxo–3–thioxo–2,3,4,5–tetrahydro–1,2,4–triazine)," Journal of Organometallic Chemistry 467:119–126 (1994).

Gleichmann et al., "η$^5$–Pentamethylcyclopentadienyl–ruthenium(II) Complexes containing η$^6$–Co–ordinated Dipeptides with Aromatic Side Chains," J. Chem. Soc. Dalton Trans. 1549–1554 (1995).

Guo et al., "Chelate ring–opening ruthenium complexes: X–ray crystal structure and solution studies of cis, trans–bis (2–dimethyl–aminoethyl)–diphe–nyl–phosphino(dichloro)ruthenium(II)," Inorganica Chimica Acta 273:1–7 (1998).

Gupta et al., "Synthesis, characterization, reactivity and structure of some mono and binuclear (η$^6$–p–cymene)ruthenium(II) complexes," Journal of Organometallic Chemistry 568:13–20 (1998).

Harvey "Metnl–Ammonia Reduction of Aromatic Molecules," Synthesis 4:161–172 (Apr. 1970).

Hung et al., "Aquo Chemistry of Monoarene Complexes of Osmium(II) and Ruthenium(II)," Inorganic Chemistry 20(2):457–463 (1981).

Jensen et al., "Facile preparation of η$^6$–p–cymene ruthenium diphosphine complexes. Crystal structure of [(η$^6$–p–cymene)Ru(dppf)Cl]PF$_6$," Journal of Organometallic Chemistry 556:151–158 (1998).

Korn et al., "Oligomeric (η$^6$–arene) ruthenium(II) complexes of adenine and adenosine with N6,N7 coordination," Inorganica Chimica Acta 254:85–91 (1997).

Krämer et al., "Application of π–Arene–Ruthenium Complexes in Peptide Labeling and Peptide Synthesis," Angew. Chem. Int. Ed. Engl. 35(11):1197–1554 (1996).

Krämer et al., "Organometallic Half–Sandwich Complexes Promote the formation of Linear Oligopeptides from Amino Acid Esters," J. Chem. Eur. 2(12):1518–1526 (1996).

McCormick et al., "Synthesis, Structure, and Disproportionation of Labile (η$^6$–C$_6$H$_6$)Ru(CH$_3$CN)$_2$CL Salts," Organometallics 12:610–612 (1993).

Morris et al., "Inhibition of Cancer Cell Growth by Ruthenium(II) Arene Complexes," J. Med. Chem. 44:3616–3621 (2001).

Müller et al., "η$^6$–Aren)(η$^4$–buta–1,3–dien)ruthenium(0)–Komplexe:Synthese and Eigenschaften sowie Kristallstruktur von (Benzol) (butadiene) ruthenium," Journal of Organometallic Chemistry 458:219–224 (1993).

Pathak et al., "Synthesis and characterization of {Ru(η$^6$–C$_6$Me$_6$)Cl$_2$)2 ($\mu$–DCBT) and its reaction with EPh$_3$ (E = P, As, Sb), 2,2'–bipyridine and ,10'–phenanthroline," Indian Journal of Chemistry 37A:165–168 (Feb. 1998).

Pertici et al., "Synthesis of the Arene Complex [RuCl$_2$(η$^6$–o–MeC$_6$H$_4$CO$_2$Me)$_2$] and Separation of its Diastereomeric (–)(S)–1–Phenylethylamine Adducts," J. Chem. Soc. Dalton Trans. 315–320 (1988).

Sava, "Ruthenium compounds in cancer therapy," Metal Compounds in Cancer Therapy Chapter 4:65–91 (1994).

Sheldrick et al., "η$^5$–Pentamethylcyclopentadienyl–ruthenium(II) complexes containing η$^6$–coordinated α–amino acids," Journal of Organometallic Chemistry 470:183–187 (1994).

Sheldrick et al., "Synthesis and Structural Characterization of η$^6$–Arene–Ruthenium(II) Complexes of α–amino acids with coordinating side chains," Journal of Organometallic Chemistry 377:357–366 (1989).

Sheldrick et al., "Synthesis and Structural Characterization of η$^6$–Arene–Ruthenium(II) Complexes of Alanine and Guanine Derivatives," Inorganica Chimica Acta 168:93–100 (1990).

Solórzano et al., "Preparation of arene Ruthenium(II) Complexes with Activated Ligands for Protein Labeling," Inorganica Chimica Acta 97:135–141 (1985).

Wolff et al., "(η$^6$–Arene)ruthenium(II) Labeling of Amino Acids and Peptides with Aromatic Side–Chains," Chem. Ber./Recueil 130:981–988 (1997).

Wolff et al., "Bis(arene) ruthenium(II) complexes containing η$^6$–coordinated phenylalanine derivatives," Journal of Organometallic Chemistry 531:141–149 (1997).

Zelonka et al., "Benzene Complexes of Ruthenium(II)," Canadian Journal of Chemistry 50:3063–3072 (1972).

* cited by examiner

HALF-SANDWICH RUTHENIUM (II) COMPOUNDS COMPRISING NITROGEN CONTAINING LIGANDS FOR TREATMENT OF CANCER

RELATED APPLICATION APPLICATION

This application is a continuation of PCT/GB00/04144, now WO 01/30790, filed Oct. 26, 2000, which also claims priority to GB Application No. 0016054.9, filed Jun. 30, 2000, and GB Application No. 9925274.4, filed Oct. 27, 1999, all of which are incorporated herein by reference.

This invention relates to ruthenium (II) compounds, to their use in medicine, particularly for the treatment and/or prevention of cancer, and to a process for their preparation.

Certain ruthenium (II) complexes have been proposed for use in treating cancer. For example, U.S. Pat. No. 4,980,473 discloses 1,10-phenanthroline complexes of ruthenium (II) and cobalt (III) which are said to be useful for the treatment of tumour cells in a subject.

Some other ruthenium (II) and ruthenium (III) complexes which have been shown to exhibit antitumour activity are mentioned in Guo et al, Inorganica Chimica Acta, 273 (1998), 1–7, specifically trans-[RuCl$_2$(DMSO)$_4$], trans-[RuCl$_2$(imidazole)$_2$]- and trans-[RuCl$_4$(indazole)$_2$]. Guo et al discloses that the most interesting feature of these complexes is their anti-metastatic activity. Clarke et at have reviewed the anticancer and in particular the antimetastatic activity of ruthenium complexes: Chem. Rev. 1999, 99, 2511–2533. Also, Sava has reveiwed the antimetastatic activity in "Metal Compounds in Cancer Therapy" Ed by S P Fricker, Chapman and Hall, London 1994, p. 65–91.

Dale et al, Anti-Cancer Drug Design (1992), 7, 3–14, describes a metronidazole complex of ruthenium (II) ie, [($\eta^6$-C$_6$H$_6$)RuCl$_2$(metronidazole)] and its effect on DNA and on *E. coli* growth rates. Metronidazole sensitises hypoxic tumour cells to radiation and appears to be an essential element of the complexes of Dale et al. There is no indication in Dale et al that the complexes would be at all effective in the absence of the metronidazole ligand.

Krämer et al, *Chem Eur J.*, 1996, 2, No. 12, p. 1518–1526 discloses half sandwich complexes of ruthenium with amino esters.

There exists a need for novel anti-cancer compounds which can be used as alternatives to the compounds which are currently available.

The present invention provides a novel class of ruthenium (II) complexes having anti-tumour activity.

According to the present invention there is provided a ruthenium (II) compound of formula (I):

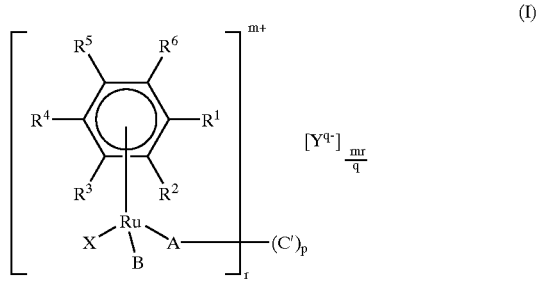

(I)

wherein:
R$^1$, R$^2$, R$^3$, R$^4$, R$^5$ and R$^6$ independently represent H, alkyl, —CO$_2$R', aryl or alkylaryl, which latter two groups are optionally substituted on the aromatic ring;

R' represents alkyl, aryl or alkaryl;
X is halo, H$_2$O, (R')(R")SO, R'CO$_2$— or (R')(R")C=O, where R" represents alkyl, aryl or alkaryl;
Y is a counterion;
m is 0 or 1;
q is 1, 2or 3;
C' is C$_1$ to C$_{12}$ alkylene, optionally substituted in or on the alkylene chain, bound to two A groups;
p is 0 or 1 and r is 1 when p is 0 and r is 2 when p is 1; and
A and B are: each independently N-donor nitrile ligands; or B is halo and A is an N-donor pyridine ligand, optionally substituted at one or more of the carbon atoms of the pyridine ring; or p is 0, A is NR$^7$R$^8$ and B is NR$^9$R$^{10}$, wherein R$^7$, R$^8$, R$^9$ and R$^{10}$ independently represent H or alkyl, and A and B are linked by an alkylene chain, optionally substituted in or on the alkylene chain; or p is 1, A is NR$^7$ and B is NR$^9$R$^{10}$, wherein R$^7$, R$^9$ and R$^{10}$ are as previously defined, and A and B are linked by an alkylene chain, optionally substituted.

The compounds of the invention may be in the form of solvates and/or prodrugs. Prodrugs are variants of the compounds of the invention which can be converted to compounds of formula (I) in vivo.

The compounds of formula (I) may have one or more chiral centres. When the compounds of formula (I) have one or more chiral centres, they may be in the form of one enantiomer, may be enriched in one enantiomer or may be a racemic mixture.

The term "alkyl" as used herein includes C$_1$ to C$_6$ alkyl groups which may be branched or unbranched and may be open chain or, when they are C$_3$ to C$_6$ groups, cyclic. Unbranched open chain alkyl groups include, for example, methyl, ethyl, propyl, butyl, pentyl and hexyl. Branched open chain alkyl groups include, for example, 2-propyl, 2-butyl and 2-(2-methyl)propyl. Cyclic groups include cyclopropyl; cyclobutyl, cyclopentyl and cyclohexyl. The alkyl groups in the compounds of the invention may optionally be substituted. Substituents include one or more further alkyl groups and/or one or more further substituents, such as, for example, cyano, nitro, hydroxyl, haloalkyl, —CO$_2$alkyl, halo, thiol (SH), thioether (eg, S-alkyl) and sulfonate. The term "alkylene" is defined similarly to the definition of the term "alkyl" but includes C$_2$ to C$_{12}$ groups and is a divalent species with radicals separated by two or more (eg, from two to twelve) carbon atoms linked in a chain. Preferably, the alkylene groups are straight chain groups. Alkylene groups are optionally substituted in the alkylene chain, preferably with one or more phenylene (eg, 1,4phenylene) and/or —CONR$^{1a}$— groups and/or —NR$^{2a}$— groups, where R$^{1a}$ and R$^{2a}$ independently represent H, alkyl, aryl or alkaryl. Preferably, R$^{1a}$ and R$^{2a}$ are H or C$_1$ to C$_3$ alkyl.

The term "aryl" as used herein includes aromatic carbocyclic rings such as phenyl and naphthyl and heterocyclic rings such as pyridyl, imidazolyl, pyrrolyl and furanyl. Aryl groups may optionally be substituted with one or more substituents including, for example, alkyl, cyano, nitro, hydroxyl, haloalkyl, —CO$_2$alkyl, halo, thiol (SH), thioether (eg, S-alkyl) and sulfonate.

The term "alkaryl" means alkyl substituted with aryl eg, benzyl.

The term "halo" means a halogen radical selected from fluoro, chloro, bromo and iodo.

The term "haloalkyl" means alkyl substituted with one or more halo groups eg, trifluoromethyl.

In the compounds of formula (I), $R^1$, $R^2$, $R^3$, $R^4$, $R^5$ and $R^6$ may represent H. Alternatively, $R^1$ may be 2-propyl and $R^4$ may be methyl, with $R^2$, $R^3$, $R^5$ and $R^6$ all representing hydrogen. As a further alternative, $R^1$ may be phenyl, with $R^2$, $R^3$, $R^4$, $R^5$ and $R^6$ all representing hydrogen. In a yet further alternative, $R^1$ may be —$CO_2R'$, such as —$CO_2CH_3$ for example, with $R^2$, $R^3$, $R^4$, $R^5$ and $R^6$ all representing hydrogen.

In one aspect, A and B in the compounds of formula (I) both represent $R^{11}$—CN. $R^{11}$ is alkyl, preferably $C_1$ to $C_3$ alkyl, more preferably methyl.

In another aspect, one of A and B in the compounds of formula (I) represents a 4-substituted pyridine and the other represents halo. The pyridine may be substituted at the 4-position by, for example, groups including nitro, cyano and $C(O)NR^{12}R^{13}$ wherein $R^{12}$ and $R^{13}$ are independently selected from H and alkyl (eg, $C_1$ to $C_6$ alkyl). The group at the 4-position of the pyridine ring is preferably an electron withdrawing group.

In a further aspect, A and B may together represent $NR^7R^8$—$(CR^{12}R^{13})_n$—$NR^9R^{10}$, wherein $R^{12}$ and $R^{13}$ are independently H or allyl or $R^{12}$ and $R^{13}$ groups, on the same carbon atom or on neighbouring carbon atoms, are linked to form a carbocylic ring and n is an integer from 1 to 4. Preferably, $R^{12}$ and $R^{13}$ are both hydrogen and n is 2 or 3, more preferably 2. $R^7$, $R^8$, $R^9$ and $R^{10}$ are preferably H or methyl and, more preferably, all of $R^7$, $R^8$, $R^9$ and $R^{10}$ are H.

When $R^8$ is present in A, then p is 0. When $R^8$ is absent, then p is 1.

In a further aspect of the invention, $R^8$ is absent from A, p is 1 and C' is $C_4$ to $C_{10}$ straight chain alkylene (eg, hexylene). Compounds according to this aspect of the invention are so-called dinuclear complexes comprising two ruthenium atoms per complex.

Other examples of dinuclear complexes of the invention are those in which is A and B together represent:

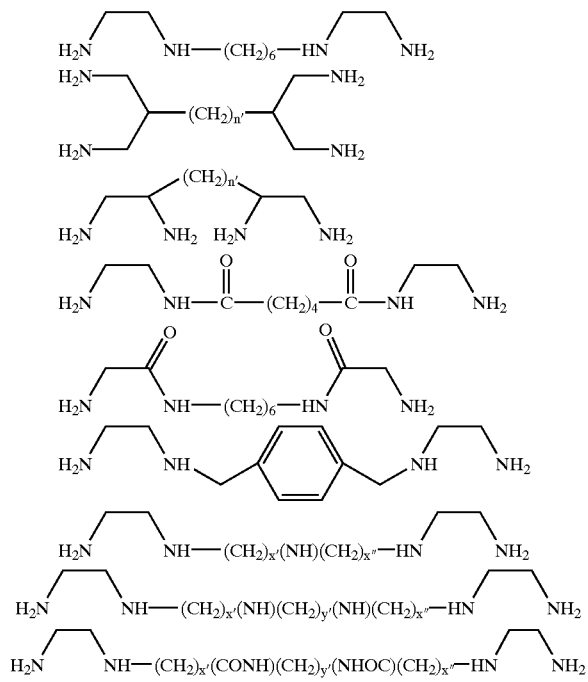

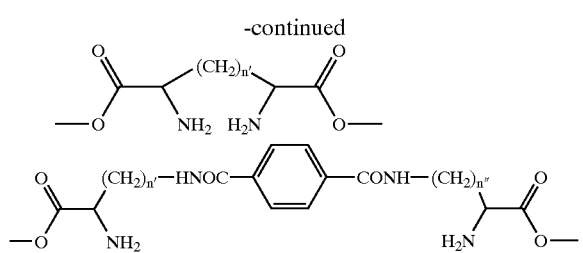

wherein each n', n", x', x" and y' independently represents an integer from 1 to 12, preferably 1 to 6.

$Y^{q-}$ in compounds of formula (I) is a counterion and is only present in the compound when the complex containing the metal ion is charged. $Y^{q-}$ is preferably a non-nucleophilic anion such as $PF_6^-$, for example.

R' and R" are preferably alkyl. Most preferably, both R' and R" are methyl.

Compounds of formula (I) may be used in medicine. In particular, compounds of formula (I) may be used to treat and/or prevent cancer.

Therefore, the present invention also provides the use of a compound of the invention (ie, a compound of formula (I)) in the manufacture of a medicament for the treatment and/or prevention of cancer.

Further provided by the invention is a method of treating and/or preventing cancer which comprises administering to a subject a therapeutically effective amount of a compound of the invention.

The compounds of the invention may be used directly against a tumour. Alternatively or additionally, the compounds may be used to prevent or inhibit metastasis and/or to kill secondary tumours. It will be understood that the prevention or inhibition of metastasis is encompassed by the term "preventing cancer", as used herein.

The invention also provides a pharmaceutical composition comprising one or more compounds of the invention together with one or more pharmaceutically acceptable excipients. Suitable excipients include diluents and/or carriers.

The compounds of the invention may be administered by a number of routes including, for example, orally, parenterally (eg, intramuscularly, intravenously or subcutaneously), topically, nasally or via slow releasing microcarriers. Thus, suitable excipients for use in the pharmaceutical compositions of the invention include saline, sterile water, creams, ointments, solutions, gels, pastes, emulsions, lotions, oils, solid carriers and aerosols.

The compositions of the invention may be formulated in unit or subunit dosage form including, for example, tablets, capsules and lozenges and containers containing the composition in a form suitable for parenteral administration.

The specific dosage level of the compounds and compositions of the invention will depend upon a number of factors, including the biological activity of the specific compound used and the age, body weight and sex of the subject. It will be appreciated that the subject may be a human or a mammalian animal.

The compounds and compositions of the invention can be administered alone or in combination with other compounds. The other compounds may have a biological activity which complements the activity of the compounds of the invention eg, by enhancing its effect in killing tumours or by reducing any side-effects associated with the compounds of the invention.

The present invention also provides a process for preparing the compounds of the invention which comprises the reaction of a compound of formula $[(\eta^6\text{-}C_6(R^1)(R^2)(R^3)(R^4)(R^5)(R^6))RuX_2]$, which may be in the form of a monomer or a dimer, with A and B, optionally in the presence of $Y^{q-}$, in a suitable solvent for the reaction, wherein $R^1$, $R^2$, $R^3$, $R^4$, $R^5$, $R^6$, X, A, B and Y are as defined above for the compounds of the invention.

Suitable compounds of formula $[(\eta^6\text{-}C_6(R^1)(R^2)(R^3)(R^4)(R^5)(R^6))RuX_2]$ for use as starting materials (starting ruthenium complexes) in the process of the invention include $[(\eta^6\text{-}C_6H_6)RuCl_2]_2$, $[(\eta^6\text{-}C_6H_6)RuBr_2]_2$, $[(\eta^6\text{-}C_6H_6)RuI_2]_2$, $[(\eta^6\text{-}p\text{-cymene})RuCl_2]_2$, $[(\eta^6\text{-}p\text{-cymene})RuBr_2]_2$ and $[(\eta^6\text{-}p\text{-cymene})RuI_2]_2$ which can be prepared by known methods eg Bennett et al, *J. Chem. Soc. Dalton Trans.*, 1974, 233.

When A and B in the compounds of the invention are $R^{11}$—CN, the solvent for the reaction may be $R^{11}$—CN itself. Preferred reaction conditions include stirring the starting ruthenium complex, as described above, in $R^{11}$—CN as solvent at room temperature until a sufficient amount of product is formed. The reaction mixture comprises a source of $Y^{q-}$, such as a compound of formula $(NH_4^+)Y^{q-}$ eg, $NH_4PF_6$.

Compounds of formula (I) in which A and B represent, together, $NR^7R^8$—$(CR^{12}R^{13})_n$—$NR^9R^{10}$ or $NR^9R^{10}$—$(CR^{12}R^{13})_n$—$NR^7$—C'—$NR^7$—$(CR^{12}R^{13})_n$—$NR^9R^{10}$ can be produced, according to the process of the invention, by stirring the starting ruthenium complex in the presence of a slight excess of $NR^7R^8$—$(CR^{12}R^{13})_n$—$NR^9R^{10}$ or an equimolar amount of $NR^9R^{10}$—$(CR^{12}R^{13})_n$—$NR^7$—C'$NR^7$—$(CR^{12}R^{13})_n$—$NR^9R^{10}$, respectively, in a suitable solvent, preferably an alcoholic solvent such as methanol. The reaction may be carried out at room temperature or at elevated temperature (eg, 30° C. to 90° C.) until a sufficient amount of product is formed; optionally after cooling the reaction mixture. The reaction mixture comprises a source of $Y^{q-}$, such as a compound of formula $(NH_4^+)Y^{q-}$ eg, $NH_4PF_6$.

Compounds of formula (I) in which A or B is an N-donor pyridine ligand may be obtained, according to the process of the invention, by heating a mixture of the starting ruthenium complex and excess pyridine compound (such as a 1.5- to 3-fold molar excess) in a suitable solvent such as benzene until a sufficient amount of product is formed. The reaction may be carried out under reflux conditions.

The precipitate which is formed in the process of the invention comprises or consists of the compound of the invention. The compound of the invention may be isolated from the reaction mixture by separating the precipitate from the liquid phase (eg, by filtration) and then removing the solvent from the precipitate (eg, under reduced pressure). The solid thus formed, which comprises or consists of the compound of the invention may, optionally, be purified eg, by recrystallisation from a suitable solvent (including, for certain compounds of the invention, acetonitrile or acetonitrile/ether (where A and B are $R^{11}$—CN and $R^{11}$ is methyl) and methanol/ether).

The following non-limiting examples illustrate the present invention.

EXAMPLES

A. Synthesis
General

The starting materials, $[(\eta^6\text{-}C_6H_6)RuCl_2]_2$, $[(\eta^6\text{-}C_6H_6)RuBr_2]_2$, $[(\eta^6\text{-}C_6H_6)RuI_2]_2$, $[(\eta^6\text{-}p\text{-cymene})RuCl_2]_2$, $[(\eta^6\text{-}p\text{-cymene})RuBr_2]_2$, $[(\eta^6\text{-}p\text{-cymene})RuI_2]_2$ were prepared as previously reported&. Acetonitrile was dried over $CaH_2$ and ethylenediamine distilled over Na metal prior to use.

The preparations of Examples 1 and 2 were based on a published synthesis[ii] and followed the same general procedure.

Example 1

Preparation of $[(\eta^6\text{-}p\text{-cymene})RuCl(CH_3CN)_2]^+[PF_6]^-$[31]

$[(\eta^6\text{-}p\text{-cymene})RuCl_2]_2$ (0.31 g, 0.51 mmol) was stirred in 20 ml reagent grade acetonitrile. $NH_4PF_6$ (0.18 g, 1.10 mmol) in 5 ml acetonitrile was added in one portion, the flask sealed without specific precautions to exclude air and the reaction stirred at room temperature. After 14 h the pale precipitate was filtered off and the orange filtrate evaporated to leave an orange solid. This was dissolved in the minimum hot acetonitrile, filtered and allowed to cool. Ether was added until precipitation was obvious and the, mixture placed in the freezer for 2 d. The precipitate was filtered, washed with ether and dried in vacuo.

Yield: 0.28 g, 0.56 mmol, 54.9%

| $C_{14}H_{20}ClF_6N_2PRu$ (497.82) | Calc. | % C = 33.78 | % H = 4.05 | % N = 5.62 |
|---|---|---|---|---|
|  | Found | % C = 33.80 | % H = 3.91 | % N = 5.53 |

Example 2

Preparation of $[(\eta^6\text{-}p\text{-cymene})RuBr(CH_3CN)_2]^+[PF_6]^-$

Procedure as in Example 1. $[(\eta^6\text{-}p\text{-cymene})RuBr_2]$ (0.24 g, 0.3 mmol), $NH_4PF_6$ (0.12 g, 0.74 mmol), dry acetonitrile (12 ml). Final product recrystallised from acetonitrile/ether as deep red crystals.

Yield: 0.28 g, 0.52 mmol, 86.67%

| $C_{14}H_{20}BrF_6N_2PRu$ (542.27) | Calc. | % C = 31.01 | % H = 3.72 | % N = 5.16 |
|---|---|---|---|---|
|  | Found | % C = 31.22 | % H = 3.75 | % N = 5.09 |

The ethylenediamine complexes of Examples 3 to 6 were prepared in the is following manner[i]:

Example 3

Preparation of $[(\eta^6\text{-}C_6H_6)RuCl(H_2NCH_2CH_2NH_2\text{—}N, N)]^+[PF_6]^-$ $[(\eta^6\text{-}C_6H_6)RuCl_2]_2$ (0.167 g, 0.33 mmol) was suspended in dry methanol (50 ml) and ethylenediamine (0.06 g, 1 mmol) added in one portion. This was stirred for 3 h, filtered and $NH_4PF_6$ (0.5 g, 3.07 mmol) added. The volume was slowly reduced to approx. 15 ml on the rotary evaporator. The product formed as a microcrystalline solid on leaving to stand at 4° C. This was collected, washed with ether and recrystallised from methanol/ether.

Yield: 0.128 g, 0.31 mmol, 46.96%

| $C_8H_{14}ClF_6N_2PRu$ (419.69) | Calc. | % C = 22.89 | % H = 3.36 | % N = 6.67 |
|---|---|---|---|---|
|  | Found | % C = 22.81 | % H = 3.24 | % N = 6.51 |

Example 4

Preparation of [(η⁶-C₆H₆)RuI(H₂NCH₂CH₂NH₂—N, N)]⁺[PF₆]⁻[31]

Procedure as in Example 3. [(η⁶-C₆H₆)RuI₂]₂ (0.48 g, 0.55 mmol), dry methanol (80 ml), ethylenediamine (0.12 g, 2 mmol), NH₄PF₆ (0.5 g, 3.07 mmol).

Yield: 0.412 g, 0.81 mmol, 73.27%

| $C_8H_{14}IF_6N_2PRu$ (511.14) | Calc. | % C = 18.80 | % H = 2.76 | % N = 5.48 |
|---|---|---|---|---|
| | Found | % C = 18.52 | % H = 2.43 | % N = 5.14 |

Example 5

Preparation of [(η⁶-p-cymene)RuCl(H₂NCH₂CH₂NH₂—N, N)]⁺[PF₆]⁻[31]

Procedure as in Example 3. [(η⁶-p-cymene)RuCl₂]₂ (0.39 g, 0.64 mmol), methanol (60 ml), ethylenediamine (0.12 g, 2.00 mmol). The reaction was stirred for 1.5 h and the green liquid filtered. NH₄PF₆ (0.52 g, 3.2 mmol) was added to the yellow filtrate and the volume reduced to 15 ml. This was left to stand at 4° C. for 6 h during which time orange crystals formed.

Yield 0.23 g, 0.48 mmol, 37.73%

| $C_{12}H_{22}ClF_6N_2PRu$ (475.81) | Calc. | % C = 30.29 | % H = 4.66 | % N = 5.88 |
|---|---|---|---|---|
| | Found | % C = 30.05 | % H = 4.41 | % N = 5.98 |

Example 6

Preparation of [(η⁶-p-cymene)RuI(H₂NCH₂CH₂NH₂—N, N)]⁺[PF₆]⁻

Procedure as in Example 3. [(η⁶-p-cymene)RuI₂] (0.34 g, 0.348 mmol), ethylenediamine (0.06 g, 1 mmol), NH₄PF₆ (0.52 g, 3.2 mmol). The volume was reduced to 15 ml and left stand at 4° C. overnight during which red crystals formed.

Yield: 0.235 g, 0.41 mmol, 59.48%

| $C_{12}H_{22}IF_6N_2PRu$ (567.26) | Calc. | % C = 25.41 | % H = 3.91 | % N = 4.94 |
|---|---|---|---|---|
| | Found | % C = 25.64 | % H = 3.72 | % N = 5.24 |

Example 7

Preparation of [(η⁶-p-cymene)RuCl₂(isonicotinamide)]

[(η⁶-p-cymene)RuCl₂] (0.129 g, 0.21 mmol) was set stirring in benzene (50 ml) and isonicotinamide (0.052 g, 0.43 mmol) added in one portion. The mixture was heated to reflux under argon for 4 h during which time a mustard coloured precipitate had formed. This was collected, washed with a little benzene and recrystallised from methanol/ether to give a red crystalline material.

Yield: 0.061 g, 0.142 mmol, 33.81%

| $C_{16}H_{20}Cl_2N_2ORu$ (428.30) | Calc. | % C = 44.87 | % H = 4.71 | % N = 6.54 |
|---|---|---|---|---|
| | Found | % C = 44.65 | % H = 4.54 | % N = 6.23 |

Example 8

Preparation of [η⁶-C₆H₅CO₂CH₃)RuCl(H₂NCH₂CH₂NH₂—N, N)]⁺[PF₆]⁻

(a) Preparation of 1,4-dihydrobenzoic acid[iv]

Benzoic acid (15.5 g, 0.13 mmol) was added to dry ethanol (100 ml) in a 1 l flask equipped with a mechanical stirrer, Dewar condenser and cooling bath (dry ice/acetone). NH₃ (600 ml) was condensed into the flask and Na metal (8.3 g, 0.36 mmol) added in small pieces over a period of 30 min. When the final blue colour was discharged the mixture was left to stir for 20 min after which time solid NH₄Cl (20 g, 0.22 mol) was carefully added. The cooling bath was removed and the NH₃ allowed to evaporate with stirring, leaving a white residue. The residue was taken up in chilled H₂O (500 ml) and acidified to about pH3 by addition of 10% HCl. This was extracted with ether (4×200 ml) and the combined ether layers washed with saturated NaCl solution (1×100 ml) and dried over MgSO₄. The ether was removed on the rotary evaporator leaving a crude oil which was distilled under reduced pressure giving a clear oil.

Yield: 13.56 g, 109 mmol, 90.8%

(b) Preparation of 3-methoxycarbonylcyclohexa-1,4-diene

Concentrated H₂SO₄ (1 ml) was added to a solution of 1,4-dihydrobenzoic acid (3 g, 23.97 mmol) in freshly dried methanol (10 ml). The reaction was heated to reflux in air for 1 h, cooled, poured into H₂O (25 ml) and extracted with ether (3×50 ml). The combined ether layers were washed with 5% Na[HCO₃] solution (50 ml) and saturated NaCl solution (50 ml) and dried over MgSO₄. The ether was removed on the rotary evaporator to leave a colourless oil which was used without further purification.

Yield: 2.60 g, 18.80 mmol, 42.8%

(c) Preparation of [(η⁶-C₆H₅CO₂CH₃)RuCl₂]₂

3-methoxycarbonylcyclohexa-1,4-diene (2.6 g, 18.80 mmol) was added to a filtered solution of RuCl₃.3H₂O (1 g, 3.80 mmol) in methanol (50 ml). The reaction was heated to reflux for 8 h under argon. The reaction was cooled, filtered and the volume reduced to 20 ml. After standing for 12 h at 4° C. the precipitate was collected, washed with a little methanol followed by ether and dried in vacuo.

Yield=1.08 g, 1.75 mmol, 93.1%

| $C_{16}H_{16}Cl_4O_4Ru_2$ (616.24) | Calc. | % C = 31.18 | % H = 2.62 |
|---|---|---|---|
| | Found | % C = 31.05 | % H = 2.39 |

(d) Preparation of [(η⁶-C₆H₅CO₂CH₃)RuCl(H₂NCH₂CH₂NH₂—N, N]⁺[PF₆]⁻

Ethylenediamine (0.09 g, 1.5 mmol) was added to a stirring suspension of [(η⁶-C₆H₅CO₂CH₃)RuCl₂]₂ (0.355 g, 0.576 mmol) in methanol (200 ml). After 4 h the orange solution was filtered and the volume reduced to 20 ml. NH₄PF₆ (0.49 g, 2.3 mmol) was added and the mixture stirred for a further minute. The sealed flask was left to stand overnight at 4° C. The precipitated yellow microcrystalline solid was collected, washed with a little methanol followed by ether and dried in vacuo.

Yield 0.22 g, 0.46 mmol, 40.0%

| $C_{10}H_{16}ClN_2O_2PF_6Ru$ (477.75) | Calc. | % C = 25.14 | % H = 3.38 | % N = 5.86 |
|---|---|---|---|---|
| | Found | % C = 25.18 | % H = 3.12 | % N = 5.50 |

Example 9

Preparation of $[(\eta^6\text{-}C_6H_5C_6H_5)RuCl(H_2NCH_2CH_2NH_2\text{—}N, N]^+[PF_6]^-$ (a) Preparation of 1,4-dihydrobiphenyl'

A solution of biphenyl (10 g, 65 mmol) in freshly dried THF (200 ml) was added to $NH_3$ (400 ml) which had been condensed under argon into a 1 l flask equipped with a Dewar condenser, cooling bath (dry-ice/acetone) and mechanical stirrer. Li wire (1.125 g, 162 mmol) was added in small pieces over a period of 15 min. After a further 15 min stirring, solid $NH_4Cl$ (15 g, 280 mmol) was added and the dark red colour discharged. The reaction was stirred at −60 ° C. for 10 min, then the cooling bath removed and the $NH_3$ allowed to evaporate under argon flow with stirring. The remaining residue was taken up in $H_2O$ (200 ml) and acidified to pH3 with 10% HCl. This was extracted with ether (4×150 ml) and the combined ether layers washed with saturated NaCl solution (1×150 ml) and dried over $MgSO_4$. The ether was removed on the rotary evaporator and the remaining oil distilled under reduced pressure (46° C., 0.2 mmHg) to give clear oil which was used without further purification.

Yield: 6.45 g, 41.26 mmol, 63.5%

(b) Preparation of $[(\eta^6\text{-}C_6H_5C_6H_5)RuCl_2]_2$ $RuCl_3\cdot3H_2O$ (2.28 g, 8.7 mmol) was dissolved in dry ethanol (25 ml) and filtered. 1,4-Dihydrobiphenyl (2.43 g, 15.5 mmol) was added in one portion and the solution heated to reflux under argon for 4 h. On cooling a brown solid settled out of solution. This was collected, washed with a little ethanol followed by ether and dried in vacuo.

Yield: 2.77 g, 8.49 mmol, 97.6%

| $C_{24}H_{24}Cl_4Ru_2$ (652.36) | Calc. | % C = 44.19 | % H = 3.71 |
|---|---|---|---|
| | Found | % C = 44.67 | % H = 3.25 |

(c) Preparation of $[(\eta^6\text{-}C_6H_5C_6H_5)RuCl(H_2NCH_2CH_2NH_2\text{—}N, N]^+[PF_6]^-$ $[(\eta^6\text{-}C_6H_5C_6H_5)RuCl_2]_2$ (0.30 g, 0.46 mmol) was refluxed in $H_2O$ (25 ml) for 1 h. At this time ethylenediamine (0.06 g, 1 mmol) was added to the refluxing suspension. The brown suspension immediately became dark green. This was refluxed for a further 30 min and filtered while hot. $NH_4PF_6$ (0.5 g, 3 mmol) was added to the yellowish filtrate and the flask briefly shaken. A yellow precipitate began to form almost immediately. The flask was sealed, allowed to cool to ambient temperature and placed in an ice-bath for 3 h. The precipitate was collected, washed with a little water, followed by ethanol, followed by ether and dried in vacuo. This was recrystallised from methanol/ether.

Yield: 0.11 g, 0.22 mmol, 23.9%

| $C_{14}H_{18}ClF_6N_2PRu$ (495.82) | Calc. | % C = 33.91 | % H = 3.66 | % N = 5.65 |
|---|---|---|---|---|
| | Found | % C = 34.06 | % H = 3.37 | % N = 5.44 |

Example 10

Preparation of $\{(\eta^6\text{-}C_6H_5C_6H_5)RuCl[H_2N(CH_2)_2NH(CH_2CH_3)]\}^+PF_6^-$ $[(\eta^6\text{-}C_6H_5C_6H_5)RuCl_2]_2$ (0.10 g, 0.158 mmol) was refluxed in water (10 ml) for 3 h and then cooled down to 80° C. To this suspension was added N-ethylethylenediamine (37 mg, 0.42 mmol) The brown suspension immediately became dark green. This was then slowly heated to reflux again for a further 1.5 h and filtered while hot. $NH_4PF_6$ (0.2 g, 1.23 mmol) was added to the yellowish filtrate and the flask briefly shaken. A yellow precipitate began to form almost immediately. After standing at 4° C. overnight, the precipitate was collected, washed with a little methanol followed by diethyl ether and dried in vacuo. This was recrystallised from methanol/ether.

Yield: 0.08 g, 0.153 mmol, 48.3%

| $C_{16}H_{22}ClF_6N_2PRu$ (523.85) | Calc. | % C = 36.68 | % H = 4.23 | % N = 5.35 |
|---|---|---|---|---|
| | Found | % C = 36.00 | % H = 4.37 | % N = 5.24 |

Example 11

Preparation of $\{[\eta^6\text{-}C_6H_5C_6H_5)RuCl]_2[H_2N(CH_2)_6NH(CH_2)_2\text{—}N,N',N'',N''']\}^{2+}2PF_6^-$ The starting material $[(\eta^6\text{-}C_6H_5C_{65})RuCl_2]_2$ was prepared as previously described. Ethylenediamine and triethylamine were freshly distilled over Na. Tetrahydrofuran (HF) was dried by distillation from Na-benzophenone. Triphenylmethyl chloride (99%) and adipoyl chloride (98%) were purchased from the Arcos Chemical Co.. All other chemicals were AR grade and were used as received.

(a) N-tritylethyldiamine

A solution of trityl chloride (5.57 g, 20 mmol) in dichloromethane (25 ml) was slowly added into a solution of ethylenediamine (8 ml, 120 mmol) in dichloromethane (75 ml) with stirring at room temperature. The addition was accomplished within 1 h and the reaction stirred overnight. The white salt was filtered off and the filtrate washed with water and dried over anhydrous sodium sulphate. Dichloromethane was removed by rotary evaporation and the residue dissolved into methanol. A white precipitate began to form after shaking for a while and the mixture was kept in the refrigerator for 5 h and then filtered off. The methanol filtrate was reduced to 10 ml and kept in the refrigerator overnight. A white solid precipitated. This was collected as the desired product and washed with diethyl ether and dried in vacuo.

Yield: 4.5 g, 14.88 mmol, 74.4%, (b) N,N'-Bis(2'tritylaminoethyl)-1,6-diamidohexane N-Tritylethyldiamine (1.5 g, 4.96 mmol) and triethylamine (1.0 g, 7.29 mmol) were dissolved in chloroform (35 ml) and cooled in an ice bath. To this solution was added adipoyl chloride (0.36 ml, 2.48 mmol) in chloroform (10 ml)

slowly with stirring. After addition, the mixture was refluxed for 2 h and cooled to room temperature. This was filtered to give a clear chloroform filtrate (see below). The filtered precipitate was dissolved into dichloromethane. This was washed with water and then saturated NaCl solution and dried over anhydrous sodium sulphate. Removal of the solvent by rotary evaporation gave a white product. The chloroform filtrate was also washed with water and saturated NaCl solution and dried over anhydrous sodium sulphate. After removal of chloroform, a further crop of product was obtained.

Yield: 1.40 g, 1.91 mmol, 77%

$C_{48}H_5O_2N_4H_2O(732.96)$

Calc. % C=78.66% H=7.15% N=7.64

Found % C=78.81% H=6.73% N=7.55

(c) N,N'-Bis(2'-tritylaminoethyl)-1,6-diaminohexane

Into a solution of N,N'-bis(2'-tritylaminoethyl)-1,6-diamidohexane (1.3 g, 1.82 mmol) in dry THF was added a suspension of $LiAlH_4$ (0.69 g, 18.18 mmol) in dry THF (20 ml) under argon with vigorous stirring. After the addition, the reaction was heated to a gentle reflux with stirring for 25 h. This was cooled to 4° C. The reaction product and excess of hydride were decomposed by the dropwise addition of $H_2O$ (0.69 ml), followed by 15% (w/v) NaOH solution (0.69 ml) and $H_2O$ (2.07 ml) in succession. After vigorous stirring for 30 min, the mixture was filtered by suction and the resulting cake was washed thoroughly with dichloromethane. The combined filtrate was concentrated to dryness on the rotary evaporator and the resulting residue dissolved into dichloromethane (50 ml). This was washed with water and then saturated NaCl solution and dried over anhydrous sodium sulphate. Removal of dichloromethane by rotary evaporator afforded a colourless solid.

Yield: 1.20 g, 1.75 mmol, 96%

(d) N,N'-Bis(2-aminoethyl)-1,6-diaminohexane tetrahydrochloride

A mixture of N,N'-bis(2'-tritylaminoethyl)-1,6-diaminohexane (1.0 g 1.45 mmol) and 6 M HCl (30 ml) was refluxed for 3 h. Then the mixture was filtered and the filtrate was concentrated to about 3 ml over vacuo. Addition of methanol into the concentrated solution afforded a white salt.

Yield: 0.46 g, 1.32 mmol, 92%

$C_{10}H_{26}N_4 \cdot 4HCl(348.09)$

Calc. % C=34.48% H=8.68% N=16.09

Found % C=34.26% H=8.77% N=16.24

(e) $\{[\eta^6\text{-}C_6H_5C_6H_5)RuCl]_2[H_2N(CH_2)_2NH(CH_2)_6NH(CH_2)_2NH_2\text{—}N,N',N'',N''']\}^{2+}2PF_6^-$ $[(\eta^6\text{-}C_6H_5C_6H_5)RuCl_2]_2$ (0.106 g, 0.162 mmol) in 10 ml water was refluxed for 2.5 h and then cooled to 50° C. Into this suspension was added a solution of N,N'-bis(2-aminoethyl)-1,6-diaminohexane (0.162 mmol) in methanol which was obtained by the treatment of N,N'-bis(2'-aminoethyl)-1,6-diaminohexane tetrahydrochloride (56.39 g, 0.162 mmol) with 1.294 ml 0.5008 N KOH—MeOH solution. The mixture was then heated to reflux for 1.5 h. This was filtered while hot. $NH_4PF_6$ (0.175 g, 1.07 mmol) was added into the bright yellow filtrate to yield a bright yellow precipitate. This was recrystallized from methanol/ether.

Yield: 0.10 g, 0.093 mmol, 57.5%

$C_{34}H_{46}Cl_2F_{12}N_4P_2Ru_2(1073.74)$

Calc. % C=38.03% H=4.32% N=5.22

Found % C=37.86% H=4.25% N=5.20

B. Biological Data

1. Protocol for Testing Ru Compounds

The compounds are tested on 24-well trays. Cells growing in a flask are harvested just before they become confluent, counted using a haemocytometer and diluted down with media to a concentration of $1 \times 10^4$ cells per ml. The cells are then seeded in the 24-well trays at a density of $1 \times 10^4$ cells per well (i.e. 1 ml of the diluted cell suspension is added to each well). The cells are then left to plate down and grow for 72 hours before adding the compounds of the invention.

The Ru complexes are weighed out and made up to a concentration of 1 mg/ml with deionised water then sonicated until they go into solution. The appropriate volume of the Ru solution is added to 5 ml of media to make it up to a concentration of 100 $\mu$M for each drug. This 100 $\mu$M solution is then serially diluted to make up the 10 $\mu$M, 1 $\mu$M and 0.1 $\mu$M solutions.

The media is removed from the cells and replaced with 1 ml of the media dosed with drug. Each concentration is done in duplicate. A set of control wells are left on each plate, containing media without drug.

The cells are left exposed to the drugs for 24 hours and then washed with phosphate buffered saline before fresh media is added.

They are allowed to grow on for a further 3 days before being counted using a Coulter counter.

Preparing Cells for Counting:

Media is removed and 1 ml of PBS is added to the cells.

250 $\mu$l of trypsin is added and cells left in incubator for a few minutes to allow the monolayers to detach.

Once trypsinised, 250 $\mu$l of media is added to each well to neutralise the trypsin. 200 $\mu$l of this suspension is added to 10 ml of NaCl for counting.

2. Results

Using the above protocol, a number of compounds of the invention were tested on A2780 ovarian cancer cell line. The results are as follows:

| Compound (Example No.) | IC50 ($\mu$M) |
| --- | --- |
| 1 | 7 |
| 2 | 8 |
| 7 | 11 |
| 5 | 8 |
| 4 | 20 |
| 3 | 8 |
| 6 | 6 |
| 9 | 6 |
| 8 | 55 |
| 10 | 6 |
| 11 | 5 |

References (i) M. A. Bennett, A. K. Smith *J. Chem. Soc. Dalton Trans.* 1974, 233; R. A. Zelonka, M. C. Baird *Can. J. Chem.* 1972, 50, 3063

(ii) F. B. McCormick, D. D. Cox, W. B. Gleason *Organomet.* 1993, 12, 610

(iii) C. Solarzano, M. A. Davis *Inorg. Chim. Acta* 1985, 97, 135

(iv) M. G. B. Drew, C. M. Regan, S. M. Nelson *J. Chem Soc. Dalton Trans.* 1981, 1034

(v) R. G. Harvey *Synthesis* 1970, No. 4, 161

What is claimed is:

1. A pharmaceutical composition comprising:
(a) a ruthenium (II) compound of formula (I):

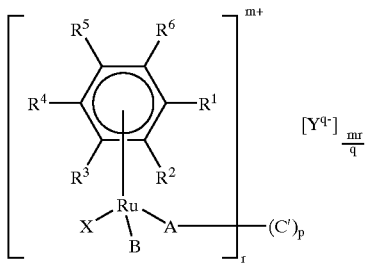

wherein:
$R^1$, $R^2$, $R^3$, $R^4$, $R^5$, and $R^6$ independently represent H, alkyl, cycloalkyl, —$CO_2R'$, aryl or alkylaryl, which latter two groups are optionally substituted on the aromatic ring;
R' represents alkyl, cycloalkyl, aryl or alkaryl;
X is halo, $H_2O$, (R')(R")SO, $R'CO_2$— or (R')(R")C=O, where R" represents alkyl, cycloalkyl, aryl or alkaryl;
Y is counterion;
m is 0 or 1;
q is 1, 2 or 3;
C' is $C_1$ to $C_{12}$ alkylene or cycloalkylene, optionally substituted in or on the alkylene or cycloalkylene chain, bound to two A groups;
p is 0 or 1 and r is 1 when p is 0 and r is 2 when p is 1; and
p is 0, A is $NR^7R^8$ and B is $NR^9R^{10}$, wherein $R^7$, $R^8$, $R^9$ and $R^{10}$ independently represent H or alkyl, and A and B are linked by an alkylene or cycloalkylene chain, optionally substituted in or on the alkylene or cycloalkylene chain; or p is 1, A is $NR^7$ and B is $NR^9R^{10}$, wherein $R^7$, $R^9$ and $R^{10}$ are as previously defined, and A and B are linked by an alkylene or cycloalkylene chain, optionally substituted; and
(b) at least one pharmaceutically acceptable excipient.

2. The composition as claimed in claim 1, wherein $R^2$, $R^3$, $R^4$, $R^5$ and $R^6$ all represent H.

3. The composition as claimed in claim 1 or 2, wherein $R^1$ is H.

4. The composition as claimed in claim 1, wherein $R^1$ is 2-propyl and $R^4$ is methyl.

5. The composition as claimed in claim 1 or 2, wherein $R^1$ is phenyl.

6. The composition as claimed in claim 1 or 2, wherein $R^1$ is —$CO_2CH_3$.

7. The composition as claimed in claim 1, wherein A and B together represent $NR^7R^8$—$(CR^{12}R^{13})_n$—$NR^9R^{10}$, wherein n is an integer from 1 to 4 and $R^{12}$ and $R^{13}$ are hydrogen, or are linked at the same or, when n is 2 to 4, at neighboring carbon atoms to form a carbocylic ring.

8. The composition as claimed in claim 7, wherein $R^7$, $R^8$, $R^9$ and $R^{10}$ all represent H.

9. The composition as claimed in claim 7 or 8, wherein $R^{12}$ and $R^{13}$ are both H and n is 2.

10. The composition as claimed in claim 7 or 8, wherein p is 0.

11. The composition as claimed in claim 7 or 8, wherein $R^8$ is absent, p is 1 and C' is $C_4$ to $C_{10}$ straight chain alkylene.

12. A method for treating ovarian cancer, comprising administering to a subject a therapeutically effective amount of a compound of formula (I)

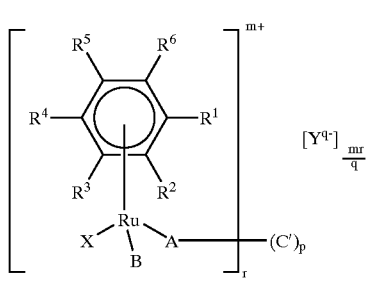

wherein:
$R^1$, $R^2$, $R^3$, $R^4$, $R^5$, and $R^6$ independently represent H, alkyl, cycloalkyl, —$CO_2R'$, aryl or alkylaryl, which latter two groups are optionally substituted on the aromatic ring;
R' represents alkyl, cycloalkyl, aryl, or alkaryl;
X is halo, $H_2O$, (R')(R")SO, $R'CO_2$. or (R')(R")C=O, where R" represents alkyl, cycloalkyl, aryl or alkaryl;
Y is counterion;
m is 0 or 1;
q is 1, 2 or 3:
C' is $C_1$ to $C_{12}$ alkylene or cycloalkylene, optionally substituted in or on the alkylene or cycloalkylene chain, bound to two A groups;
p is 0 or 1 and r is 1 when p is 0 and r is 2 when p is 1; and
p is 0, A is $NR^7R^8$ and B is $NR^9R^{10}$, wherein $R^7$, $R^8$, $R^9$ and $R^{10}$ independently represent H or alkyl, and A and B are linked by an alkylene or cycloalkylene chain, optionally substituted in or on the alkylene or cycloalkylene chain; or p is 1, A is $NR^7$ and B is $NR^9R^{10}$, wherein $R^7$, $R^9$ and $R^{10}$ are as previously defined, and A and B are linked by an alkylene or cycloalkylene chain, optionally substituted.

* * * * *